(12) United States Patent
Chia et al.

(10) Patent No.: US 7,153,133 B1
(45) Date of Patent: Dec. 26, 2006

(54) DISPOSABLE PROPHY ANGLE FOR AN ELECTRIC TOOTH POLISHER

(75) Inventors: Hui-Tsu Chia, No. 7, Alley 2, Lane 164, Sec. 1, Hsiafu Rd., Tucheng City (TW); Shui-Tao Tseng, Zhongshan (CN); Philip Phung-I Ho, 2780 State St., Suite#7, Santa Barbara, CA (US) 93105

(73) Assignees: Hui-Tsu Chia, Taipei Hsien (TW); Meditech International Co., Ltd., Zhongshan (CN); Philip Phung-I Ho, Santa Barbara, CA (US)

( * ) Notice: Subject to any disclaimer, the term of this patent is extended or adjusted under 35 U.S.C. 154(b) by 0 days.

(21) Appl. No.: 11/248,280

(22) Filed: Oct. 13, 2005

(51) Int. Cl.
   *A61C 3/06* (2006.01)
(52) U.S. Cl. .................................... 433/125
(58) Field of Classification Search ............... 433/125, 433/126, 114, 112
   See application file for complete search history.

(56) References Cited

U.S. PATENT DOCUMENTS 5,348,473 A * 9/1994 Kivlighan, Jr. ............. 433/114
6,168,433 B1 * 1/2001 Hamlin ....................... 433/125

* cited by examiner

*Primary Examiner*—Melba Bumgarner
(74) *Attorney, Agent, or Firm*—Rabin & Berdo, P.C.

(57) ABSTRACT

A disposable prophy angle for an electric tooth polisher, having a handle and a polishing head, has a body and a transmission assembly. The body is mounted to the handle and has a cavity and a bent distal segment. The transmission assembly is mounted in the cavity and has a rotatable driving shaft, a rotatable head mount and multiple linkage shafts. The driving shaft has multiple mounting holes. The head mount is connected to the polishing head and has multiple mounting holes. Each linkage shaft has two segments rotatably and slidably extending into a corresponding mounting hole in the driving shaft and a corresponding hole in the head mount, respectively. The linkage shafts are simple and small so the corresponding bent distal segment of the body holding the linkage shafts is also small. Therefore, the disposable prophy angle can be easily inserted into and moved around in a person's mouth.

4 Claims, 7 Drawing Sheets

DISPOSABLE PROPHY ANGLE FOR AN ELECTRIC TOOTH POLISHER

BACKGROUND OF THE INVENTION

1. Field of the Invention

The present invention relates to a tooth cleaner, and more particularly to a disposable prophy angle for an electric tooth polisher. The disposable prophy angle is compact and is easy to insert into and move around in a person's mouth to polish teeth.

2. Description of the Related Art

Electric tooth polishers are generally tools used by dentists to polish teeth.

With reference to FIG. 9, a conventional electric tooth polisher has a controller (70), a handle (80), a disposable prophy angle (90) and a head (93).

The controller (70) is connected to a power source and has a display and a switch.

The handle (80) is connected to the controller (70) through a cable and has a motor.

With further reference to FIGS. 10 and 11, the disposable prophy angle (90) is hollow, is connected to the handle and has a cavity, a bent distal segment (901), a driving shaft (91) and a driven cylinder (92). The driving shaft (91) is mounted in the cavity, is connected rotatably to the motor and has a gear (911) in the bent distal segment (901). The driven cylinder (92) rotatably engages the driving shaft (91) and has a gear (921) and a mount. The gear (921) of the driven cylinder (92) is mounted in the cavity, corresponding to the distal segment (901) and engages the gear (911) of the driving shaft (91). The mount extends out of the disposable prophy angle (90).

The head (93) is mounted to the mount of the driven cylinder (92) and rotates when driven by the motor. When the tooth polisher is used, the head (93) is coated with a special polishing paste. The head (93) rotates and contacts the teeth to polish the surface of the teeth.

However, the gears (911, 921) occupy a sizable amount of space in the cavity at the distal end (901) of the disposable prophy angle (90). This requires the distal segment (901) to be of a considerable size, which hinders the movement of the disposable prophy angle (90) in a person's mouth. The driving shaft (91) must also be perpendicular to the driven cylinder (92) due to the restriction of the angle of engagement of the gears (911, 921). In addition, the driving shaft (91), the driven cylinder (91) and the integral gears (911, 921) are made by injection molding, which adds to the cost. Furthermore, the gears (911, 921) may easily disengage from each other when the motor operates at high speed.

To overcome the shortcomings, the present invention provides a disposable prophy angle for an electric tooth polisher to mitigate or obviate the aforementioned problems.

SUMMARY OF THE INVENTION

The main objective of the invention is to provide a disposable prophy angle for an electric tooth polisher. The disposable prophy angle is compact and is easy to insert into and move around in a person's mouth to polish teeth.

The disposable prophy angle in accordance with the present invention is mounted to an electric tooth polisher having a handle and a polishing head.

The disposable prophy angle has a body and a transmission assembly.

The body is mounted to the handle and has a cavity and a bent distal segment.

The transmission assembly is mounted in the cavity and has a rotatable driving shaft, a rotatable head mount and multiple linkage shafts. The driving shaft has multiple mounting holes. The head mount is connected to the polishing head and has multiple mounting holes. Each linkage shaft has two segments rotatably and slidably extending into a corresponding mounting hole in the driving shaft and a corresponding hole in the head mount, respectively.

Other objectives, advantages and novel features of the invention will become more apparent from the following detailed description when taken in conjunction with the accompanying drawings.

DETAILED DESCRIPTION OF PREFERRED EMBODIMENT

Figure 1:
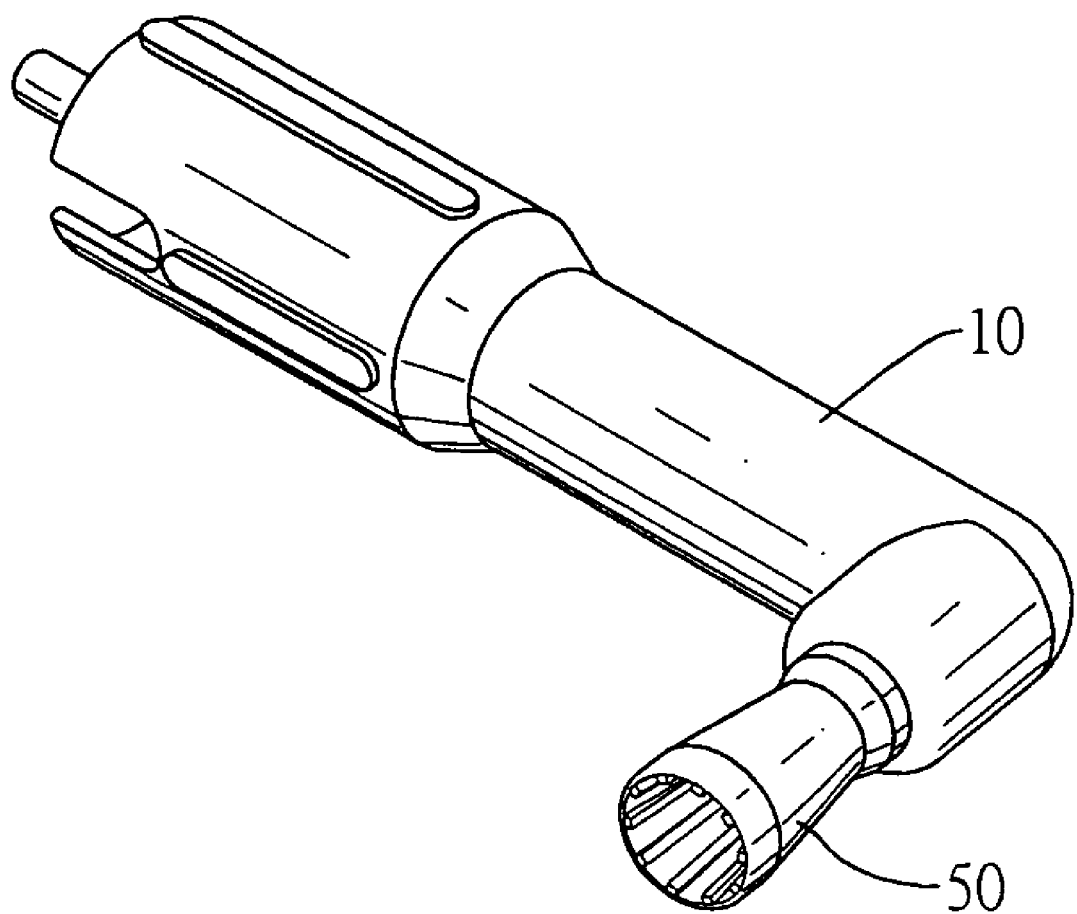
FIG. 1 is a perspective view of a disposable prophy angle for an electric tooth polisher with a head mounted to the disposable prophy angle.
Figure 2:
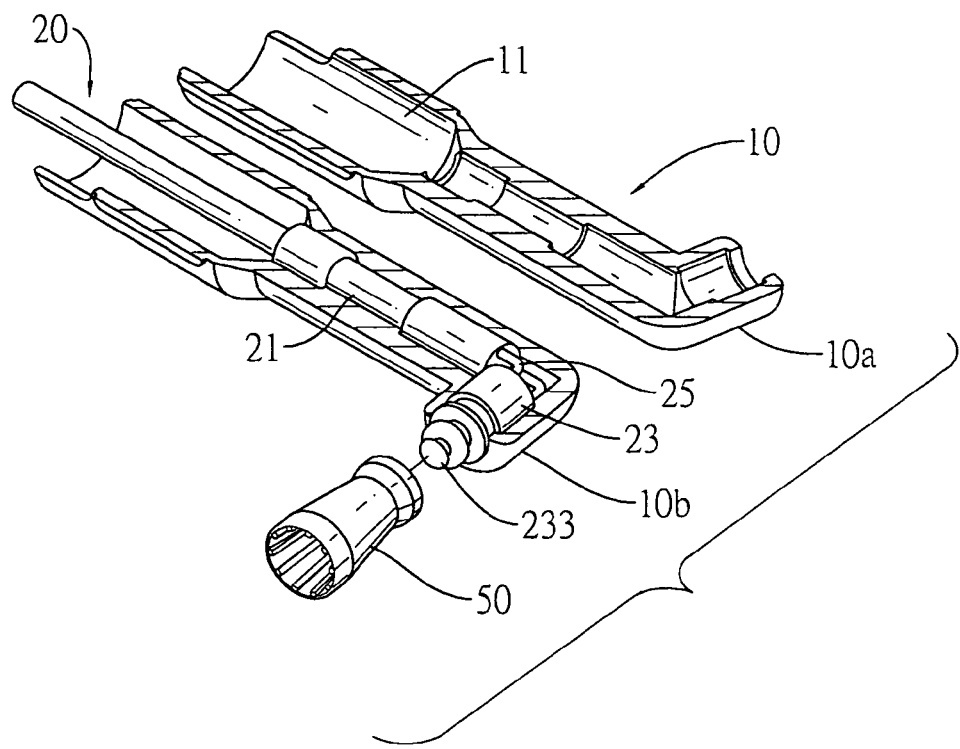
FIG. 2 is an exploded perspective view of the disposable prophy angle in FIG. 1.

With reference to FIGS. 1 and 2, a disposable prophy angle in accordance with the present invention is mounted to an electric tooth polisher. The electric tooth polisher has a controller, a handle. The controller is connected to a power source. The handle is connected to the controller through a cable and has a motor. A polishing head (50) is mounted to the disposable prophy angle The disposable prophy angle in accordance with the present invention is mounted detachably to the handle, is connected to the polishing head (50) to polish teeth in a person's mouth and has a body (10) and a transmission assembly (20).

Figure 3:
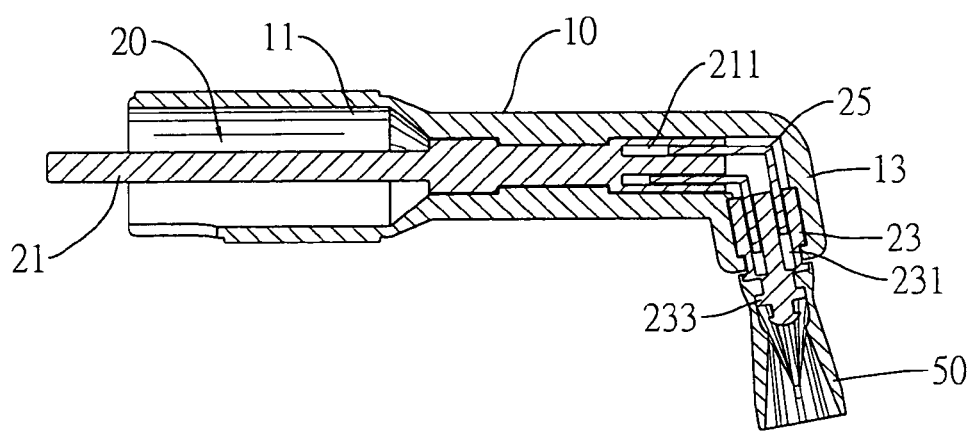
FIG. 3 is a cross-sectional side view of the disposable prophy angle in FIG. 1.

With further reference to FIG. 3, the body (10) is hollow, is mounted to the handle, may be comprised of two casing halves (10*a*, 10*b*) and has a cavity (11), a proximal open end, a distal open end and a bent distal segment (13). The cavity is defined in the body (10). The proximal and distal open ends communicate with the cavity (11). The bent distal segment (13) is bent at a preferred obtuse angle so the disposable prophy angle can be easily inserted into and moved along the teeth in a person's mouth when the electric tooth polisher is in use.

The transmission assembly (20) is mounted in the cavity (11) in the body (10), is driven by the motor and has a driving shaft (21), a head mount (23) and multiple linkage shafts (25).

The driving shaft (21) is mounted rotatably in the cavity (11) in the body (10) and has a proximal end, a distal end and multiple mounting holes (211). The proximal end of the driving shaft (21) is connected to the motor, which drives the driving shaft (21). The mounting holes (211) are defined longitudinally in the distal end of the driving shaft (21).

The head mount (23) is mounted rotatably in the cavity (11) of the body (10), corresponds to the bent distal segment (13) and has a proximal end, a distal end (233) and multiple mounting holes (231). The distal end (233) extends out of the distal open end of the body (10) and is mounted detachably to the polishing head (50). The mounting holes (231) are defined longitudinally in the proximal end of the head mount (23) and correspond to the mounting holes (211) in the driving shaft (21).

Figure 4:
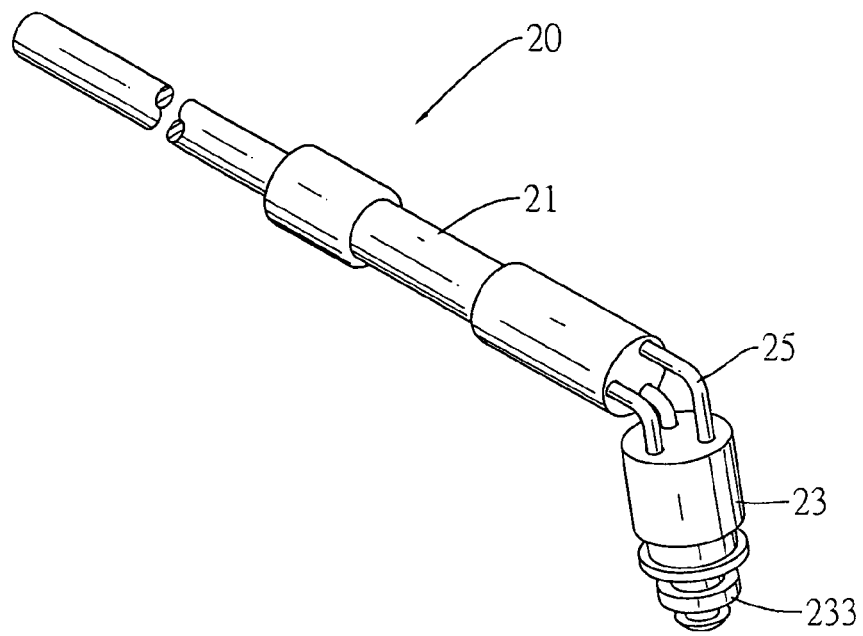
FIG. 4 is a perspective view of a transmission assembly in the disposable prophy angle in FIG. 1.
Figure 5:
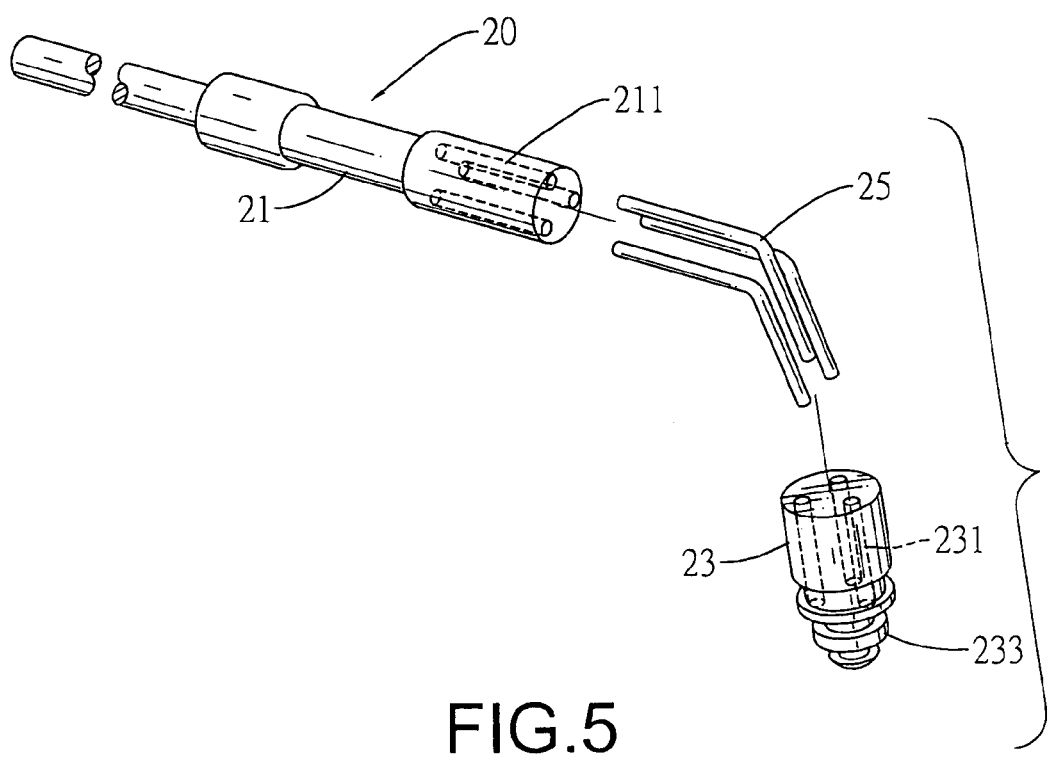
FIG. 5 is an exploded perspective view of the transmission assembly in the disposable prophy angle in FIG. 4.
Figure 6:
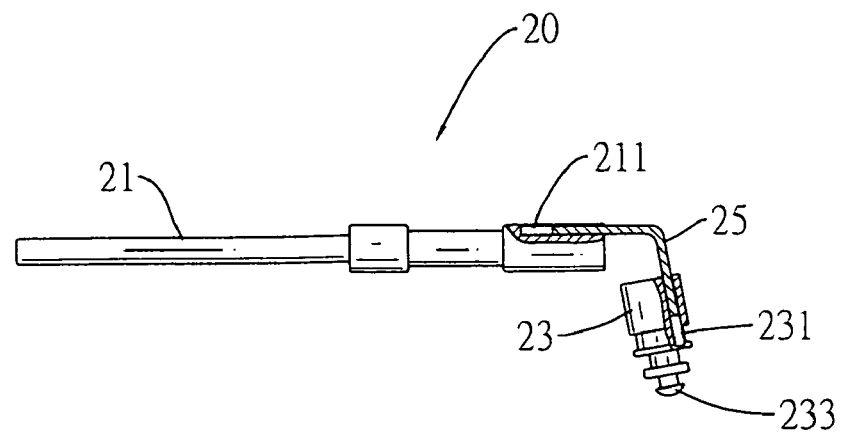
FIG. 6 is an operational side view in partial section of the transmission assembly of the disposable prophy angle in FIG. 4.
Figure 7:
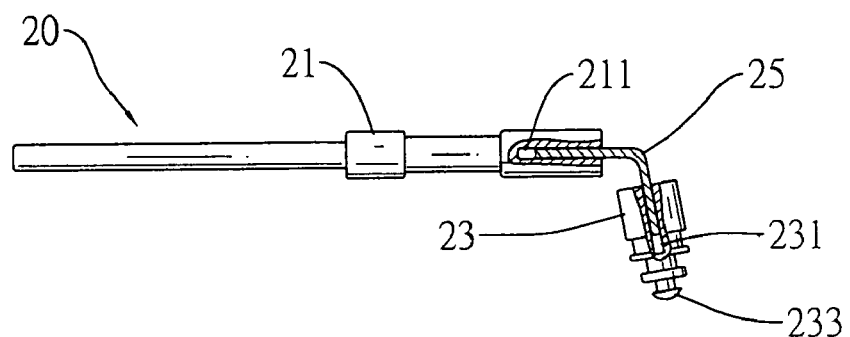
FIG. 7 is an operational side view in partial section of the transmission assembly of the disposable prophy angle in FIG. 6.
Figure 8:
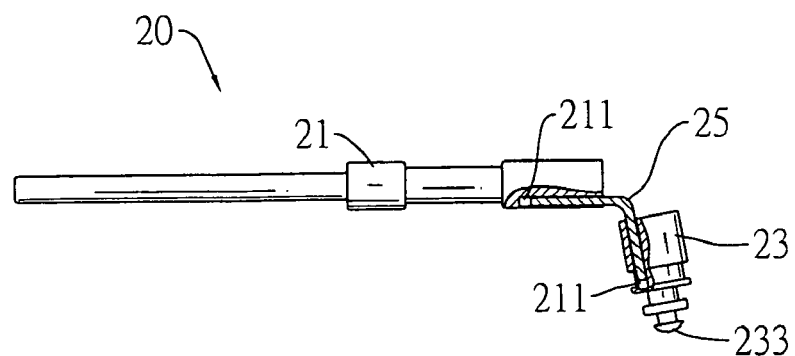
FIG. 8 is an operational side view in partial sectional of the transmission assembly of the disposable prophy angle in FIG. 7.
Figure 9:
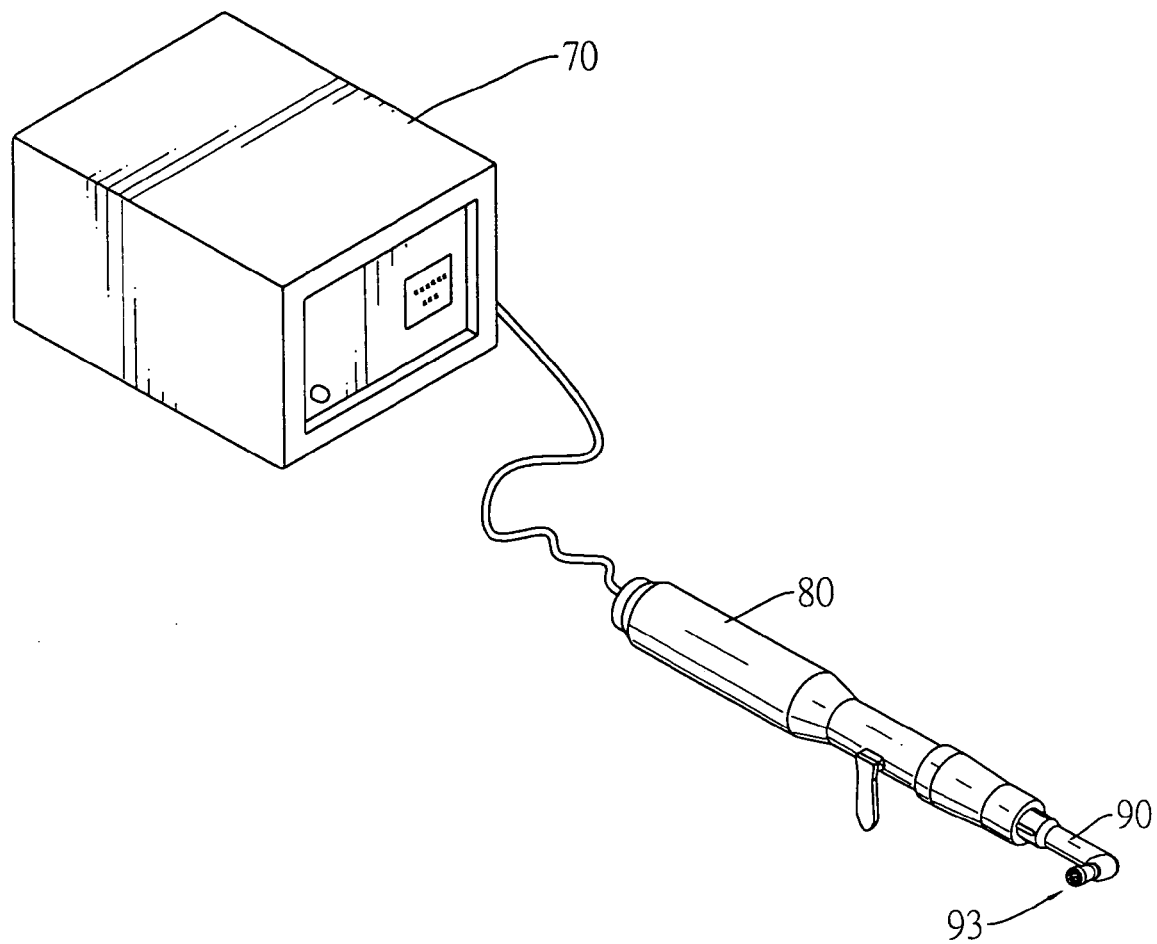
FIG. 9 is a perspective view of a conventional electric tooth polisher in accordance with the prior art.
Figure 10:
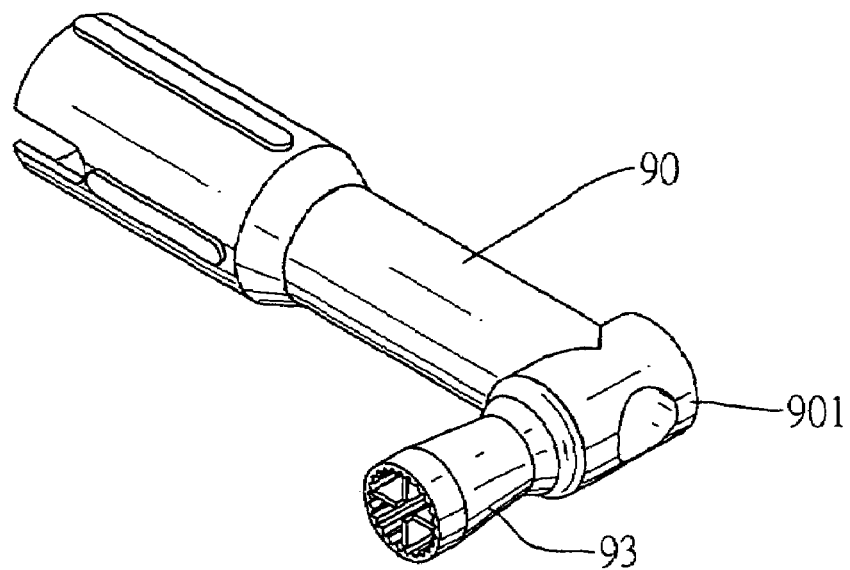
FIG. 10 is a perspective view of the disposable prophy angle of the tooth polisher in FIG. 9.
Figure 11:
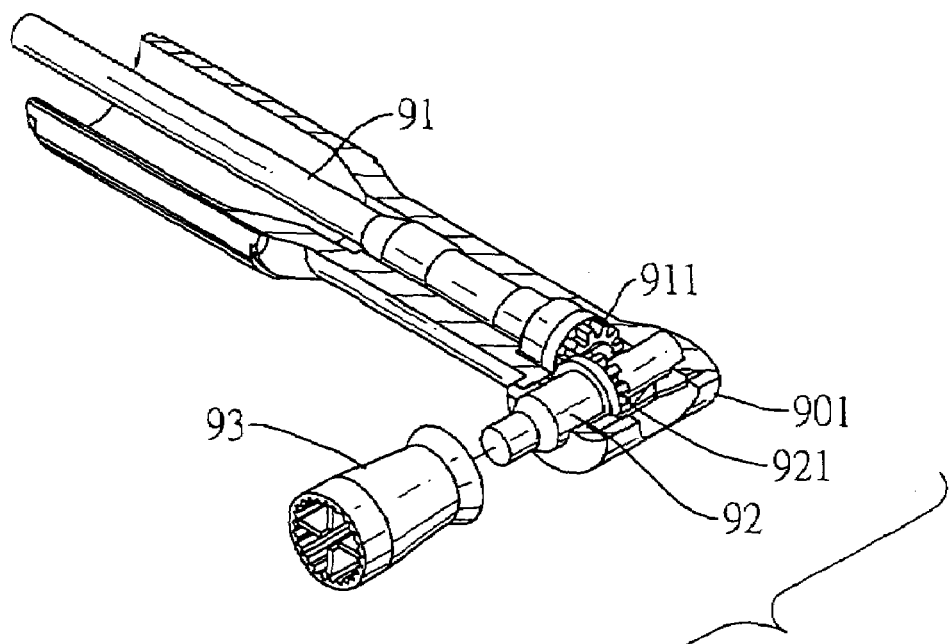
FIG. 11 is an exploded perspective view of the disposable prophy angle in FIG. 10.
Figure 12:
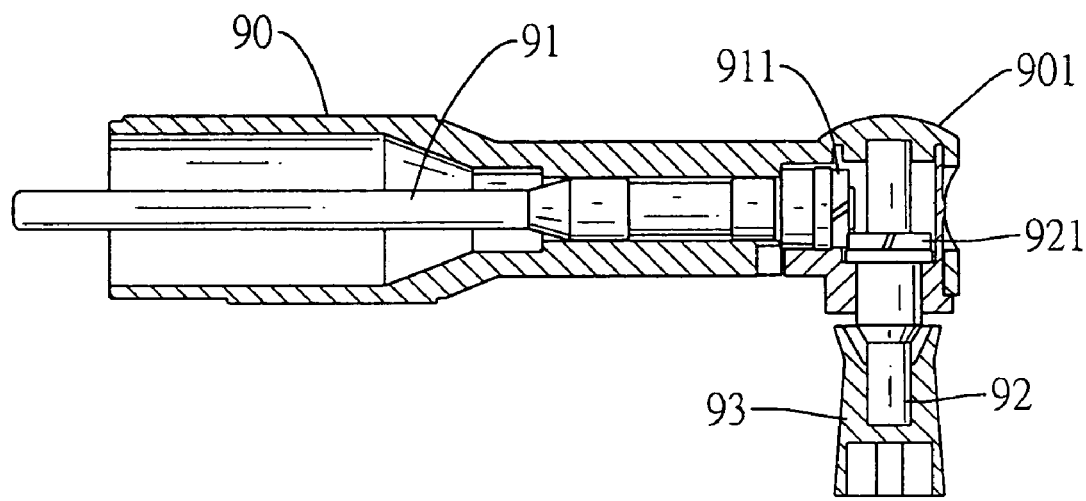
FIG. 12 is a side view in partial section of the disposable prophy angle in FIG. 10.

With reference to FIGS. 4 and 5, the linkage shafts (25) are bent, rigid and inflexible, may be made of metal, are mounted in the cavity (11), correspond to the bent distal segment (13) of the body (10) and are rotatably and slidably connected to the driving shaft (21) and the head mount (23). Each linkage shaft (25) has two segments. The segments of each linkage shaft (25) are formed with each other at an angle corresponding to the angle of the bent distal segment (13) of the body (10). The angle between the segments is preferred to be an obtuse angle. The segments rotatably and slidably extend into a corresponding mounting hole (211) in the driving shaft (21) and a corresponding hole in the head mount (23), respectively. With reference to FIGS. 6 to 8, the segments of a linkage shaft (25) move in and out of the mounting holes (211, 231) as the driving shaft (21) rotates. The depth to which the segments of one linkage shaft (25) extend into the corresponding mounting holes (211, 231) in the driving shaft (21) and the head mount (23) depends on the position of the linkage shaft (25) relative to the driving shaft (21) as it rotates. The segments of the linkage shaft (25) extend the shallowest respectively in the mounting holes (211, 231) when the linkage shaft (25) is the farthest away from the distal end of the driving shaft (21) and extend the deepest respectively when the linkage shaft (25) is the closest. Therefore, as the driving shaft (21) rotates, the segments of the linkage shafts (25) are caused to move in and out of the mounting holes (211, 231), which in turn causes the head mount (23) and polishing head (50) to rotate.

The linkage shafts (25) are simple and small so the corresponding bent distal segment (13) of the body (10) holding the linkage shafts (25) is also small. Therefore, the disposable prophy angle can be easily inserted into and moved around in a person's mouth. In addition, the linkage shafts (25) can be made by a simple cutting process and, without the need for injection molding, are cheaper. The angle between the segments of the linkage shaft (25) can be changed freely and is not restricted to 90 degrees. Furthermore, the linkage shaft (25) is connected safely and securely to the driving shaft (21) and the head mount (23) and cannot be easily disengaged.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A disposable prophy angle adapted to be mounted to an electric tooth polisher, the electric tooth polisher having a controller connected to a power source, a handle connected to the controller through a cable and having a motor and a polishing head mounted to the disposable prophy angle, wherein the disposable prophy angle comprises:
    a body adapted to be mounted to the handle and having
        a cavity defined in the body;
        a proximal open end communicating with the cavity;
        a distal open end communicating with the cavity; and
        a bent distal segment bent at an angle; and
    a transmission assembly mounted in the cavity in the body, adapted to be driven by the motor and having
        a driving shaft mounted rotatably in the cavity in the body and having
            a proximal end adapted to be connected to the motor;
            a distal end; and
            multiple mounting holes defined longitudinally in the distal end of the driving shaft;
        a head mount mounted rotatably in the cavity of the body, corresponds to the bent distal segment and having
            a proximal end;
            a distal end extending out of the distal open end of the body and adapted to be mounted detachably the polishing head; and
            multiple mounting holes defined longitudinally in the proximal end of the head mount and corresponding to the mounting holes in the driving shaft; and
        multiple bent linkage shafts being rigid and inflexible, mounted in the cavity, corresponding to the bent distal segment of the body and rotatably and slidably connected to the driving shaft and the head mount, and each linkage shaft having two segments formed with each other at an angle corresponding to the angle of the bent distal segment of the body and rotatably and slidably extending into a corresponding mounting hole in the driving shaft and a corresponding hole in the head mount, respectively.

2. The disposable prophy angle as claimed in claim 1, wherein the linkage shafts are made of metal.

3. The disposable prophy angle as claimed in claim 2, wherein the bent distal segment of the body is bent at an obtuse angle, and the angle between the segments of each linkage shaft is an obtuse angle.

4. The disposable prophy angle as claimed in claim 3, wherein the body is comprised of two casing halves.

* * * * *